United States Patent [19]
Fotsis et al.

[11] Patent Number: 5,643,900
[45] Date of Patent: Jul. 1, 1997

[54] METHOD FOR TREATMENT OF PATHOLOGICAL CONDITIONS ASSOCIATED WITH ANGIOGENESIS AND PREPARATION THEREFOR

[76] Inventors: Theodore Fotsis, Heidelbergerstrasse 54 B, D-69151 Neckargemund, Germany; Herman Adlercreutz, Riskutie 13, FIN-00950, Helsinki, Finland; Lothar Schweigerer, Lutherstrasse 6, 35033, Marburg, Germany

[21] Appl. No.: 405,776

[22] Filed: Mar. 17, 1995

Related U.S. Application Data

[63] Continuation-in-part of Ser. No. 84,969, Jul. 2, 1993, abandoned.

[51] Int. Cl.⁶ .................................................. A61K 31/56
[52] U.S. Cl. .................................................. 514/182
[58] Field of Search ..................................... 514/182

[56] References Cited

PUBLICATIONS

Seegers et al, J. Steroid Biochem, vol. 32, No. 6, pp. 797–809, 1989.

*Primary Examiner*—Jerome D. Goldberg
*Attorney, Agent, or Firm*—Birch, Stewart, Kolasch & Birch, LLP

[57] ABSTRACT

The present invention relates to a method and a composition for the treatment of pathological conditions associated with enhanced angiogenesis. The method comprises administering 2-methoxyestradiol to a subject in need of such treatment.

3 Claims, 6 Drawing Sheets

METHOD FOR TREATMENT OF PATHOLOGICAL CONDITIONS ASSOCIATED WITH ANGIOGENESIS AND PREPARATION THEREFOR

This application is a continuation-in-part of application Ser. No. 08/084,969 filed on Jul. 2, 1993, now abandoned, the entire contents of which are hereby incorporated by reference.

FIELD OF INVENTION

The present invention relates to a method for the treatment of pathological conditions associated with enhanced angiogenesis, is particular a method for the treatment and suppression of angiogenesis sustained tumor growth in a mammal. The present invention also relates to a pharmaceutical composition for use in the method of treatment.

BACKGROUND OF THE INVENTION

Angiogenesis, the generation of capillaries, is virtually absent in healthy adult organism and is restricted to a few conditions including wound healing and the formation of corpus luteum, endometrium and placenta. The endothelial cell plays a key role in the formation of new capillaries, and the neovascularization process occurs via a series of sequential steps, which are similar regardless of the nature of the inducing stimulus. These steps can be summarized as follows: the endothelial cells that line existing microvessels focally degrade the basement membrane through a finely-tuned elaboration of proteolytic enzymes and their inhibitors, and form tiny sprouts which invade the perivascular connective tissue. As these sprouts elongate by migration of endothelial cells below the tip, a luman is gradually formed. The hollow sprouts thus generated anastomose with each other to form capillary loops through which blood begins to flow. New sprouts then arise from each loop and eventually give rise to an entire capillary network.

Under normal physiological conditions in the healthy adult mammal, during cyclical changes in the female reproductive tract or in response to wounding, the coordinated sequential cellular events leading to new capillaries are spatially and temporally restricted so that the disturbed balance between naturally occurring inducers and inhibitors of neovascularization rapidly reverts to the normal situation, in which inhibitory influences predominate.

In contrast thereto, in certain pathological conditions angiogenesis is dramatically enhanced and is no longer self-limited, i.e. a result of well-balanced activity of angiogenesis inhibitors and stimulators. Pathological angiogenesis is seen during the development and progression of many diseases, such as in rheumatoid arthritis, psoriasis and diabetic retinopathy. These diseases were recently called angiogenic diseases and share at least two characteristics in common: 1) an abnormality of capillary blood vessel growth is the principal pathological feature and 2) the possibility that therapeutic control of the abnormal capillary growth would ameliorate or eliminate other manifestations of the disease. Probably the clinically most important manifestation of pathological angiogenesis is that induced by solid tumors [Folkman, J. (1985) Adv. Cancer Res. 43, 175–203 and Nature Medicine, vol. 1, number 1, (1995)]. If a neoplasm is to grow progressively as a solid mass consisting of layers of living cells more than a few millimeters thick, it must induce nearby capillaries to sprout and develop a new vascular network around and within the tumor. The new vascular network supplies the tumor with vital nutrients and oxygen and provides a removal route for toxic products of the active cell metabolism. Furthermore, new tumor vessels provide a port of exit for tumor cells to metastize to distant sites. Thus, the progressive growth of a solid tumor to develop into a life-threatening malignancy is strictly dependent on angiogenesis.

Estradiol, the major ovarian estrogen, has been extensively studied with regard to its physiological and pharmacological effects, and its involvement in endocrine-dependent carcinogenesis. On the contrary, very little is known about the contribution to the total estrogen expression of the more than 20 estrogen metabolites which are present in the female organism [Fotsis, T., Adlercreutz, H., J. Steroid Biochem., 28, 203 (1987); Fotsis T., Steroid. Biochem. 28, 215 (1987)]. Even less is known about their pharmacological effects and almost nothing about their effects on endothelial cells and angiogenesis.

SUMMARY OF THE INVENTION

According to the invention it has now surprisingly been discovered that a metabolite of estrogen, i.e. 2-methoxyestradiol (1,3,5(10)-estratrien-2,3,17β-triol 2-methylether), which has previously been thought to be an inactive metabolite, exerts a strong inhibitory effect on angiogenesis. Thus the invention provides for a method for the treatment of pathological angiogenesis and of angiogenic diseases, such as angiogenesis-sustained solid tumors, by administration to a mammal, such as a human, suffering therefrom, a pharmaceutically effective, angiogenesis inhibiting amount of 2-methoxyestradiol. The amounts contemplated by the invention are non-cytotoxic, but provide a cytostatic and reversible effect. The term "angiogenic disease" includes any pathological condition associated with enhanced angiogenesis, that is a condition which is directly or indirectly supported, sustained or aggravated by enhanced angiogenesis.

Thus the present invention is primarily directed to a method for the treatment of angiogenesis-sustained solid tumors in a mammal, such as a human. As all solid tumors are dependent on enhanced angiogenesis to grow, the treatment of the invention is generally applicable on any solid tumor. Especially contemplated treatments according to the invention include i.a. treatment of tumors of the prosrata, breast, endometrium, lung, colon, kidney, hemangiomas, sarcomas, and melanomas and skin tumors, including also metastasizing tumors, as well as the treatment of psoriasis, rheumatoid arthritis, psoriasis and diabetic retinopathy. It is also conceivable to couple 2-methoxyestradiol to another substance, such as an antibody, and thus achieve a targeted effect, at low dosage levels.

The present invention is further directed to a preparation for use in the treatment of conditions associated with enhanced angiogenesis, especially for the treatment and suppression of solid tumors, the preparation including as the active agent, an effective amount of 2-methoxyestradiol together with a pharmaceutically acceptable carrier and optionally other pharmaceutically acceptable adjuvants.

DETAILED DESCRIPTION OF THE INVENTION

According to the invention, 2-methoxyestradiol is administered to a subject in need thereof, in an amount which is at least angiogenesis-inhibiting, but lower than the cytotoxic amount. We have in the tests presented later shown that an angiogenesis-inhibiting but still non-cytotoxic amount of 2-methoxyestradiol in mice is 100 mg/kg body weight/day, which can be regarded as an upper limit in the treatment of the invention. However, in a human it is possible to use lower doses, even as low as 0.0015 mg/kg/day up to 20 mg/kg/day. The lower dose range is especially applicable when the drug is administered parenterally, for example in targeted form, e.g. coupled to an antibody, whereas the upper range applies to the other forms of administration. Especially the invention contemplates the use of a dose range, as calculated for a person weighing 70 kg, of from about 0.1 mg/day to 100 mg/day (about 0.0015 to 1.5 mg/kg body weight/day), such as 10 to 100 mg/day (about 0.15 to 1.5 mg/kg body weight/day), the latter range especially when administered orally.

2-Methoxyestradiol may be administered using any pharmaceutically acceptable form of administration. Suitable routes of administration include the oral route, such as in the form of capsules, tablets, granules, suspensions, the rectal route, such as in the form of suppositories, the parentoeal route, such as by injection or infusion, or the topical route in the form of creams, lotions, or in the form of transdermal delivery systems.

Any pharmaceutically acceptable vehicle or carrier as well as adjuvants for the manufacture, dissolution and administration of the preparation may be used in the drug delivery system, and are as such well known to the person skilled in the art. Also the amount of active agent included in the dosage form can be well determined by a person skilled in the art, and is dependant on the form of administration as well as the severity of the condition being treated.

In order to show the beneficial effects of 2-methoxyestradiol, the following tests were carried out.

TEST REPORT

In connection with the test carried out.

In the first tests the effects of the most important estrogen metabolites were studied on bFGF-induced proliferation of low density bovine capillary endothelial cells (BBCE) in vitro. In the tests, BBCE cells were adjusted to a density of 5.000 cells per ml in DMEM plus 10% newborn calf serum and seeded in 1 ml aliquots per well into 12-well cluster dishes. The cells received every other day bFGF (2.5 ng/ml) and either only buffer (10 µl) or buffer containing increasing concentrations of 2-methoxyestradiol. Cells were counted after 6 days with a Coulter particle counter. The results are expressed as IC 50-values, i.e., the concentration of the respective substance resulting in half the number of cells compared to that of the control (cells receiving bFGF and buffer only, usually in the range of 200.000 cells per well). The values are the means of duplicate determinations which varied by <10% of the mean.

The results obtained were:

| Trivial name | Systematic name | IC 50 (µM) |
| --- | --- | --- |
| 2-Methoxyestradiol | 1,3,5(10)-Estratriene-2,3,17β-triol 2-methyl ether | 0.134 |
| 2-Hydroxyestrone | 1,3,5(10)-Estratrien-2,3-diol-17-one | 5.9 |

-continued

| Trivial name | Systematic name | IC 50 (µM) |
| --- | --- | --- |
| 4-Methoxyestradiol | 1,3,5(10)-Estratriene-3,4-17β-triol 4-methyl ether | 7.24 |
| 2-Methoxyestradiol 3-methyl ether | 1,3,5(10)-Estratriene-2,3,17β-triol 3-methyl ether | 7.78 |
| 2-Methoxyestrone | 1,3,5(10)-Estratriene-2,3-diol-17-one 2-methyl ether | 11.5 |
| 2-Hydroxyestradiol | 1,3,5(10)-Estratriene-2,3,17β-triol | 15.7 |
| 2-Methoxyestriol | 1,3,5(10)-Estratriene-2,3,16α,17β-tetrol 2-methyl ether | 21.3 |
| 2-Hydroxyestradiol 3-methyl ether | 1,3,5(10)-Estratriene-2,3,17β-triol 3-methyl ether | 21.42 |
| Estrone | 1,3,5(10)-Estratrien-3-ol-17-one | 26 |
| 16-Epiestriol | 1,3,5(10)-Estratriene-3,16β,17β-triol | 31 |
| 16α-Hydroxyestrone | 1,3,5(10)-Estratrien-2,16α-diol-17-one | 31.1 |
| Estriol | 1,3,5(10)-Estratriene-3,16α,17β-triol | 32 |
| Estradiol-17β | 1,3,5(10)-Estratriene-3,17β-diol | 34.5 |
| 15α-Hydroxyestriol | 1,3,5(10)-Estratriene-3,15α,16α,17β-tetrol | n.i. |
| Estriol-16α-glucoronide | 1,3,5(10)-Estratriene-3,16α,17β-triol 16α-glucosiduronate | n.i. | n.i.: no inhibition

From this initial evaluation, it was evident that 2-methoxyestradiol exhibited the strongest inhibitory effect of all metabolites tested, the half-maximal concentration being approx. 0.15 µM.

The inhibition appeared to be very specific to the 2-methoxestradiol molecule as isomeric and very closely related structures were 40 to 250 times less potent with some estrogen metabolites having no effect at all.

The inhibitory effect of 2-methoxyestradiol was essentially the same (data not shown) on a number of different bovine and human endothelial cells lines of both capillary and arterial origin (Bovine aorta BAE, bovine adrenal cortex ACE and BME, human vein umbilical HUVE and human skin HSE), the half-maximal doses varying between 0.2 and 2.5 µM. 2-Methoxyestradiol produced a cytostatic and reversible (data not shown) inhibition of proliferating endothelial cells at concentrations up to 3–5 µM, being increasingly cytotoxic (reduction of cell number below the initial seeding density) at higher doses.

Figure 1:
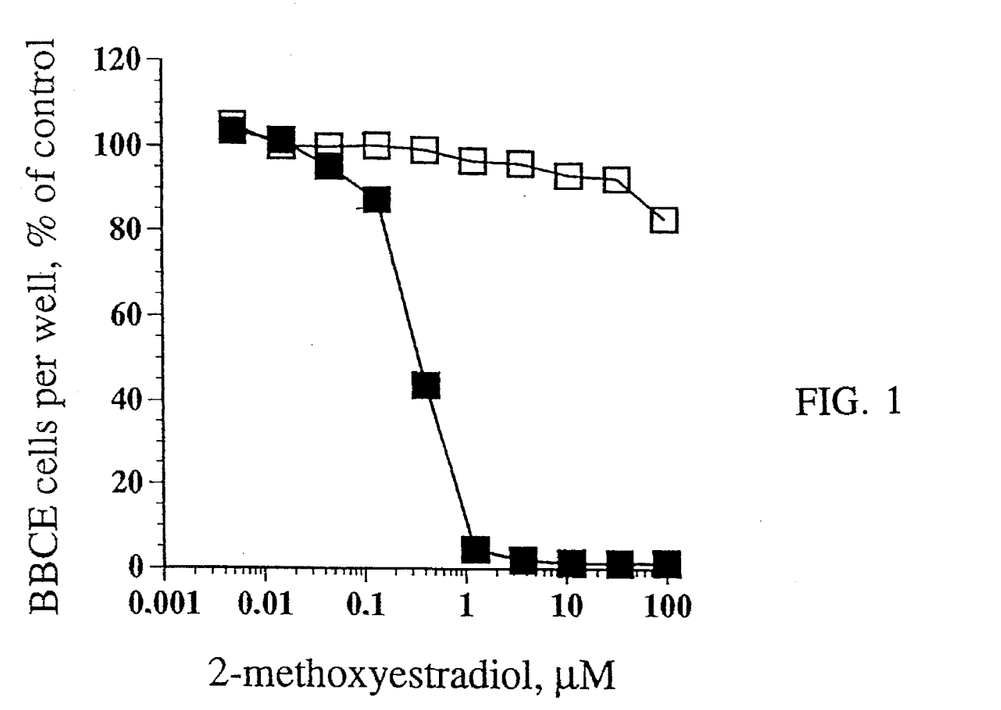
FIGS. 1 and 3 show the effect of cell density on the activity of 2-methoxyestradiol on the proliferation on endothelial cells (BBCE) and fibroblasts (HFK2), respectively, FIGS. 2A–2E relate to results from in vitro tests for inhibition of angiogenesis, and FIGS. 4A–4D relate to results from in vivo tests for inhibition of angiogenesis.
Figure 2A:
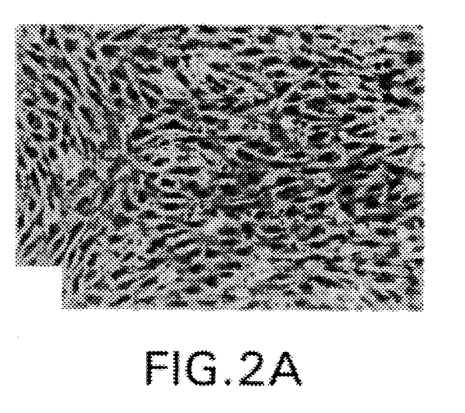
Figure 2B:
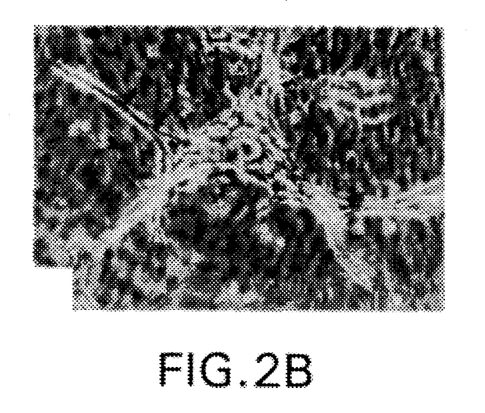
Figure 2C:
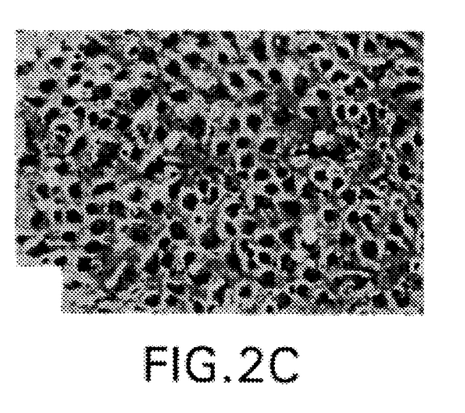
Figure 2D:
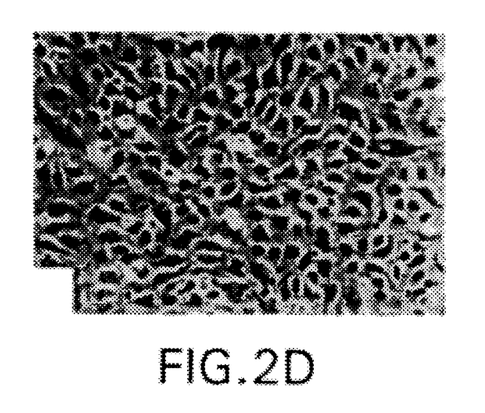
Figure 2E:
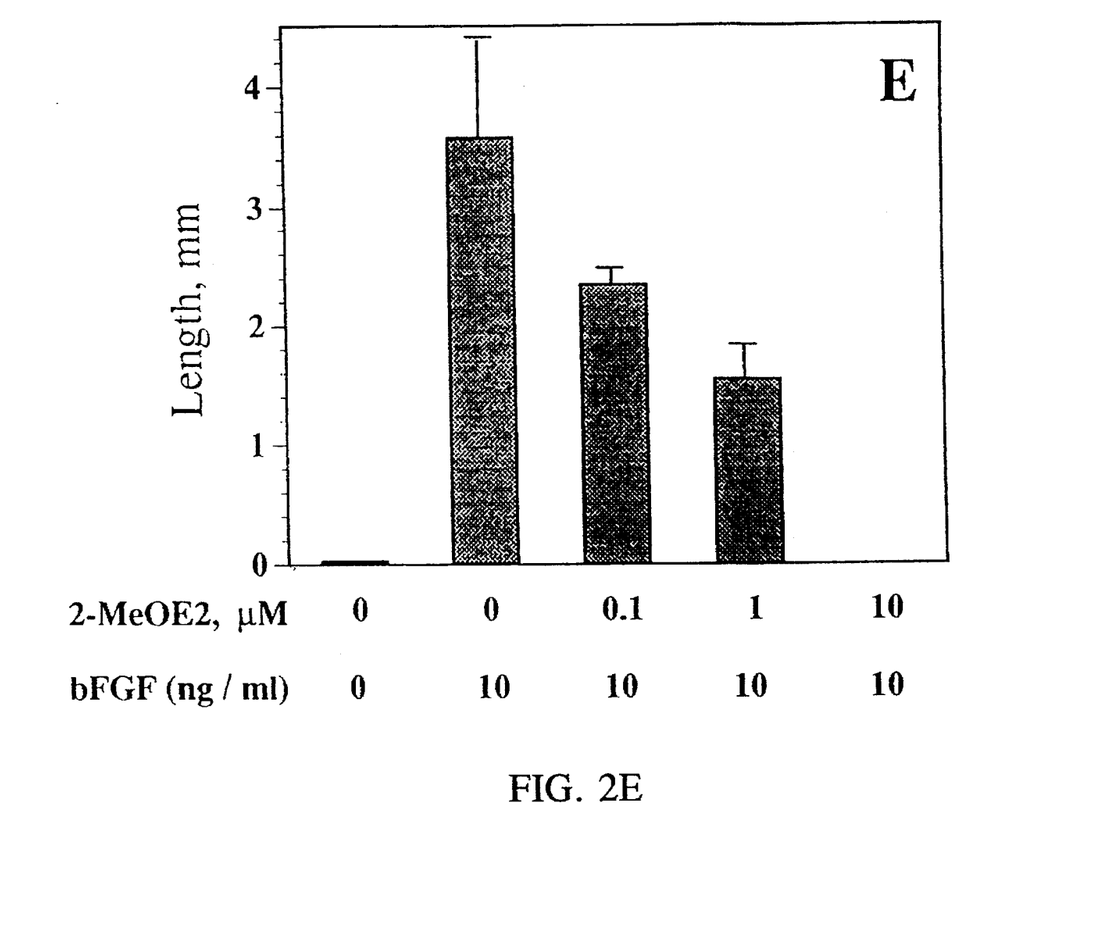

In the appended FIG. 1, the effect of cell density on the activity of 2-methoxyestradiol on the proliferation of endothelial cells is shown. BBCE cells were suspended in DMEM containing 10% newborn calf serum in one-ml aliquots containing either 15.000 (■) or 100.000 (□) cells, respectively, into 12-well dishes. BBCE cells seeded at 15.000 per ml received every other day bFGF (2.5 ng/ml medium) plus either only buffer (controls) or the indicated concentrations of 2-methoxyestradiol when seeded at a density of 100.000 per ml, the BBCE cells were left to grow to confluence. The medium was then changed and the cells received either buffer (controls) or the indicated concentrations of 2-methoxyestradiol. In all experiments, substances were added as 10 µl aliquots and cells were counted after 6 days. Values are expressed as percent of control (cells receiving no 2-methoxyestradiol) and are the means of duplicate determinations which varied by <10% of the mean.

This test showed that low density, fast proliferating endothelial cells were inhibited by 2-methoxyestradiol whereas confluent cultures of endothelial cells were totally unaffected by this compound; a marginal cytotoxicity was observed at 100 µM. It appears, therefore, that 2-methoxyestradiol targets only growth factor-stimulated cells. Quiescent, unstimulated endothelial cells are essentially unaffected by 2-methoxyestradiol.

In addition to the effects on proliferation, 2-methoxyestradiol inhibits the in vitro migration of BBCE cells. In this test, a confluent monolayer of endothelial cells is wounded by a razor blade and then the number of endothelial cells migrating to the wounded area in 12 hours are counted. 2-methoxyestradiol inhibited the migration of BBCE cells to the wounded area in doses similar to those that inhibited also the proliferation of these cells. This property is very important for angiogenesis. New capillaries can not be formed unless the endothelial cells have the ability to migrate to and in the extracellular space. There, they align forming solid cords; formation of a lumen eventually occurs when such cords sprouting from adjacent capillaries meet each other.

Migration to the extracellular space requires that the endothelial cells are able to penetrate the basic membrane of the capillary. Lysis of the dense extracellular matrix is further required for migration in the extracellular space. Endothelial cells achieve this invasive phenotype by producing proteolytic enzymes that degrade both the basic membrane and components of the extracellular matrix. Thus, co-ordinated proliferation, invasion and migration of endothelial cells result in formation of new capillaries, a process which is called angiogenesis. These phenomena are initiated by angiogenic factors like bFGF and can be studied in in vitro models that mimic the in vivo situation. In these in vitro angiogenesis assays endothelial cells are first cultured to confluence on top of a collagen gel. When such confluent endothelial monolayers are stimulated by bFGF, they invade the underlying collagen gel and form capillary-like structures within it. 2-Methoxyestradiol inhibited such in vitro angiogenesis (FIGS. 2A–E).

In this test, BME cells were gown to confluence on three-dimensional collagen gels. After confluence, they receive either no additions (A), bFGF (10 ng/ml) only (B), 2-methoxyestradiol (10 µM) only (C), or 2-methoxyestradiol (10 µM) 2 h prior to bFGF (10 ng/ml) (D). Fresh medium and compounds were added every 2–3 days, and the cultures photographed and fixed after 7 days (magnification=125×). In B, the lumina of the tubules are evident as translucent slits under phase contrast microscopy (arrows); in D, 2-methoxyestradiol inhibits the formation of such tubes. In C, 2-methoxyestradiol alone causes a more polygonal morphology of endothelial cells comparing to the culture in A. In E, a quantitative analysis of the results demonstrated in A–D is presented. Confluent cultures of BME cells were treated for 7 days as described in A–D. Fields measuring 1×1.4 mm were then randomly selected and photographed, and BME cell invasion was quantified. 2-Methoxyestradiol at 0.1, 1, and 10 µM reduced the bFGF-induced invasion of BME by 35%, 57% and 100% respectively, with a half maximal inhibition at approximately 0.35 µM. Results are expressed as the mean length in mm±SEM from three photographic fields per well. A single representative experiment is shown; this experiment has been repeated 4 times.

Figure 3:
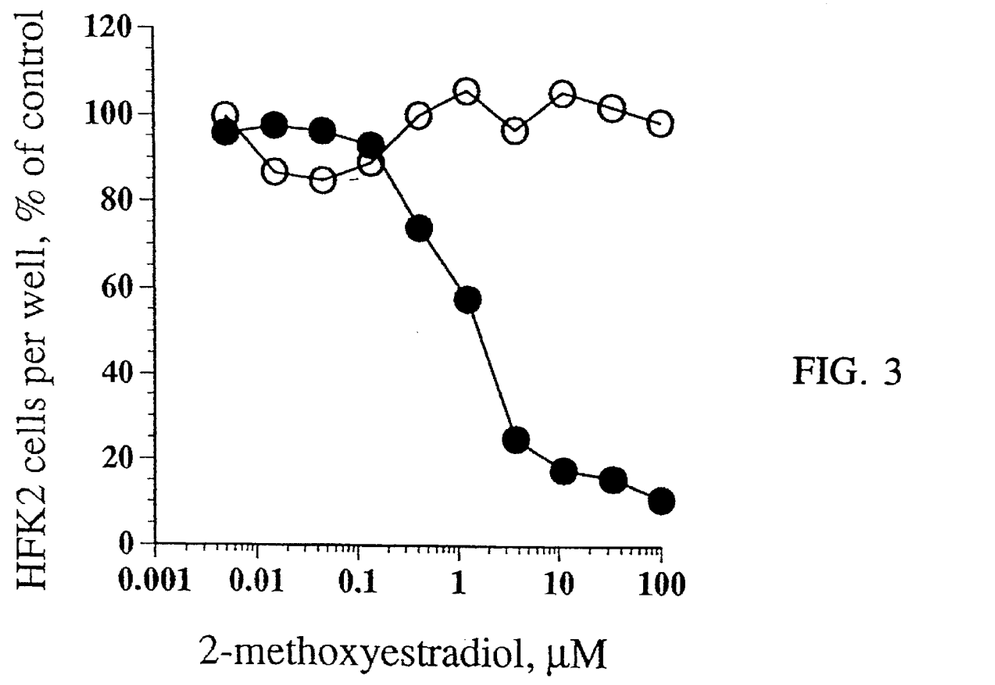

Endothelial cells are not the only target of 2-methoxyestradiol. The sensitivity of low density cultures of various normal (bovine granulosa BG, mouse embryonic fibroblasts 3T3-NIH and human skin fibreblasts HFK2) and malignant cell lines (human neuroblastoma SH-EP, human rhabdomyosarcoma A204 and human retioblastoma YM79) was not significantly different from that of endothelial cells; the half-maximal concentrations were between 0.35 to 2.2 µM (FIG. 3 and data not shown). Again quiescent, confluent monolayers of fibroblasts (HFF2) were totally unaffected at doses up to 100 µM (FIG. 3). The result indicates that actively proliferating cells are the target of 2-methoxyestradiol and that the compound probably interferes with a proliferation-associated cellular event.

Figure 4A:
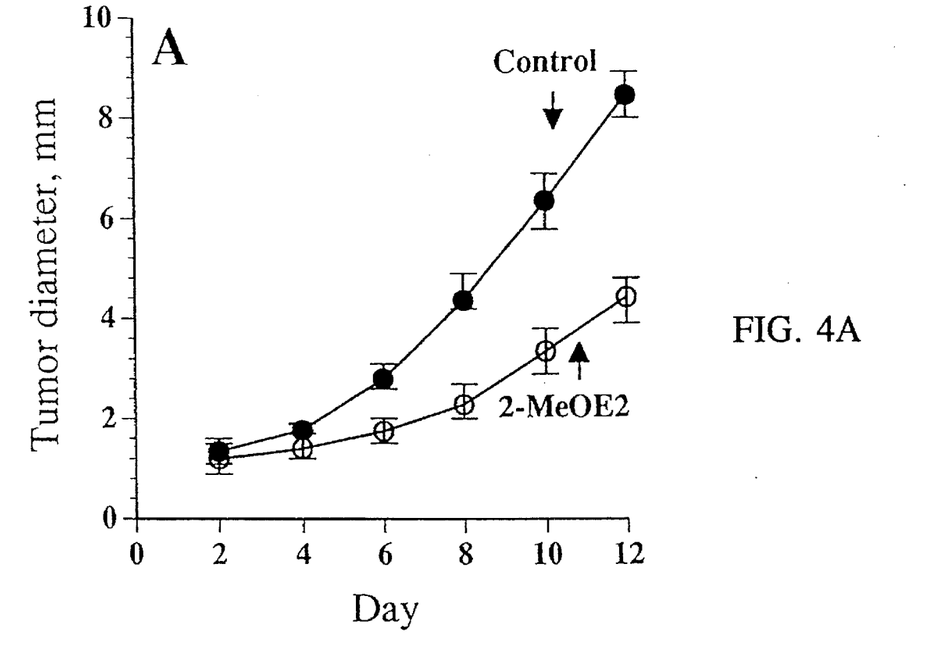
Figure 4B:
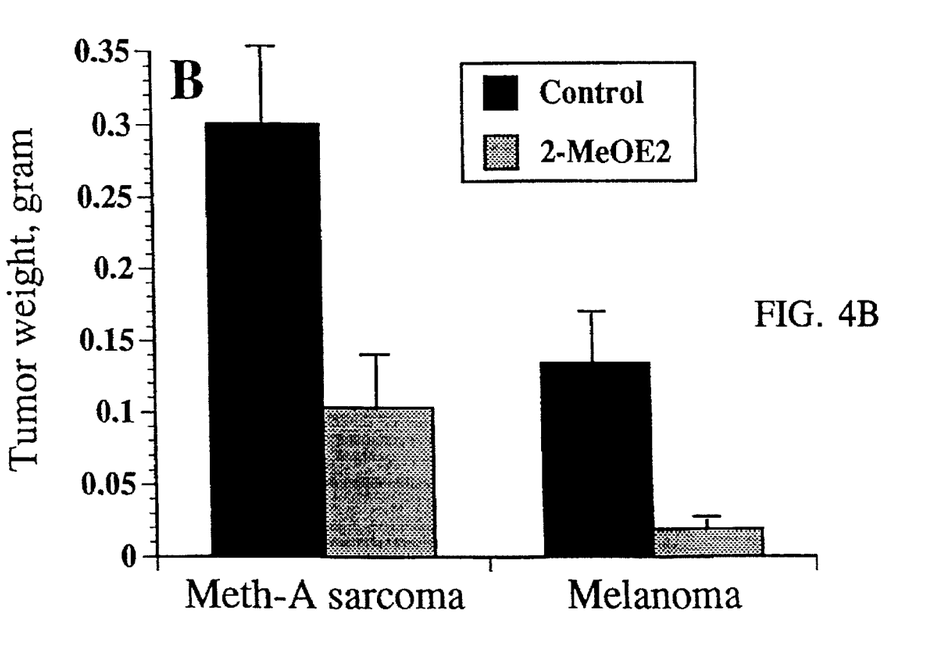
Figure 4C:
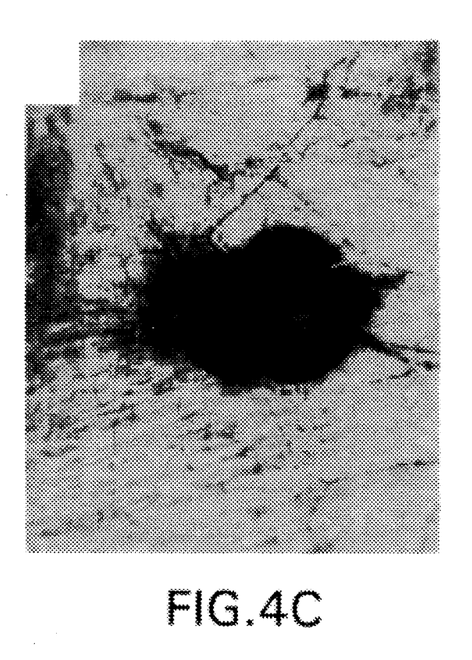
Figure 4D:
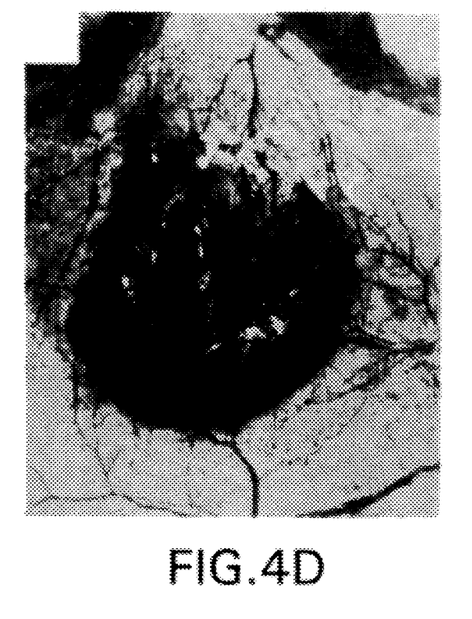

The in vitro effects of 2-methoxyestradiol on angiogenesis and proliferation of malignant cells prompted us to investigate the in vivo properties of the compound. We have postulated that 2-methoxyestradiol could influence the growth of tumors both directly, by inhibiting the division of tumor cells, and indirectly, by inhibiting the tumor-induced angiogenesis. Solid tumors can not grow beyond a diameter of 1–2 mm unless they stimulate the formation of new capillaries. 2-Methoxyestradiol, administered orally in mice, inhibited the growth of Meth A sarcoma and melanoma tumors (FIGS. 4A and B) and significantly reduced the tumor vasculature (FIGS. 4C and D).

In this in vivo test, Meth-A sarcoma and melanoma cells ($1\times10^6$) were inoculated subcutaneously in 0.1 ml saline in the same position of the dorsal skin of C3H mice (n=20). On the same day, the mice received orally either 2-methoxyestradiol, at 100 mg per kg in body weight, suspended in 300 µl of olive oil (n=10) or 300 µl olive oil alone (n=10). This treatment was carried our every day and the diameter of the tumors was monitored every second day. On day 12 the mice were sacrificed and the tumor weights were measured. In A, the time course of the growth of the Meth-A sarcoma tracts, expressed as diameter in mm±range, is depicted, and B, the weight in grams of both the Meth-A sarcoma and melanoma tumors on day 12 is presented. In a small number of control and 2-methoxyestradiol mice, the dorsal skin, together with the tumor, was excised and the angiogenesis within the subcutaneous fascia in the control (C) and treated (D) mice was visualized with indian ink. Magnification by 10. Apart from their marginally lower weight (approx. 15%), the treated mice exhibited no apparent signs of toxicity and were all alive after 12 days of daily treatment. The lack of toxicity is in agreement with the in vitro results showing no effect on quiescent, non-dividing cells (FIGS. 1 and 3).

2-Methoxyestradiol thus has potent pharmacologically properties which can be applied in the treatment of solid tumors and angiogenic diseases.

We claim:

1. Method of suppressing the growth of solid tumors sustained by angiogenesis in a mammal comprising administering to said mammal 2-methoxyestradiol in an amount of 0.0015 to 100 mg/kg body weight/day.

2. The method according to claim 1, wherein the amount administered is from 0.0015 to 1.5 mg/kg body weight/day.

3. The method according to claim 1, wherein the amount administered orally is 0.15 to 1.5 mg/kg body weight/day.

* * * * *

UNITED STATES PATENT AND TRADEMARK OFFICE
CERTIFICATE OF CORRECTION

PATENT NO. : 5,643,900
DATED : July 1, 1997
INVENTOR(S) : Fotsis et al.

It is certified that error appears in the above-identified patent and that said Letters Patent is hereby corrected as shown below:

Column 2,
Line 44, please replace "prosrata" with -- prostate --.

Signed and Sealed this

Twelfth Day of March, 2002

Attest:

JAMES E. ROGAN
Attesting Officer
Director of the United States Patent and Trademark Office